United States Patent
Ostiguy, Jr. et al.

[11] Patent Number: 5,935,175
[45] Date of Patent: Aug. 10, 1999

[54] ACETABULAR PROSTHESIS WITH RING LOCK MECHANISM

[75] Inventors: Pierre S. Ostiguy, Jr., Rochester; Robert E. Sommerich, Norton, both of Mass.

[73] Assignee: Johnson & Johnson Professional, Inc., Raynham, Mass.

[21] Appl. No.: 09/039,033

[22] Filed: Mar. 13, 1998

[51] Int. Cl.⁶ .................................................. A61F 2/32
[52] U.S. Cl. ............................................................ 623/22
[58] Field of Search ........................................ 623/22, 23

[56] References Cited

U.S. PATENT DOCUMENTS

| | | | |
|---|---|---|---|
| 4,172,296 | 10/1979 | D'Errico | 3/1.912 |
| 4,619,658 | 10/1986 | Pappas et al. | 623/22 |
| 4,650,491 | 3/1987 | Parchinski | 623/22 |
| 4,770,658 | 9/1988 | Geremakis | 623/22 |
| 4,784,663 | 11/1988 | Kenna | 623/22 |
| 4,795,469 | 1/1989 | Oh | 623/22 |
| 4,936,861 | 6/1990 | Muller et al. | 623/22 |
| 4,969,910 | 11/1990 | Frey et al. | 623/22 |
| 5,049,158 | 9/1991 | Engelhardt et al. | 623/22 |
| 5,171,285 | 12/1992 | Broderick | 623/22 |
| 5,217,499 | 6/1993 | Shelley | 623/22 |
| 5,263,988 | 11/1993 | Huebner | 623/22 |
| 5,314,487 | 5/1994 | Schryver | 623/22 |
| 5,314,491 | 5/1994 | Thongpreda | 623/22 |
| 5,360,451 | 11/1994 | Keller | 623/22 |
| 5,376,122 | 12/1994 | Pappas et al. | 623/22 |
| 5,425,779 | 6/1995 | Schlosser et al. | 623/22 |
| 5,443,519 | 8/1995 | Averill et al. | 623/22 |
| 5,507,826 | 4/1996 | Besselink et al. | 623/22 |
| 5,549,698 | 8/1996 | Averill et al. | 623/22 |
| 5,658,348 | 8/1997 | Rohr, Jr. | 623/22 |
| 5,766,260 | 6/1998 | Whiteside | 623/22 |
| 5,782,930 | 7/1998 | Lin | 623/23 |
| 5,800,555 | 9/1998 | Gray | 623/22 |

FOREIGN PATENT DOCUMENTS

| | | | |
|---|---|---|---|
| 2684544 | 6/1993 | France | 623/22 |

*Primary Examiner*—Michael J. Milano
*Attorney, Agent, or Firm*—Nutter, McClennen & Fish, LLP

[57] ABSTRACT

An acetabular prosthesis has a shell component that is implantable within bone and a liner component that is matable to the shell by a locking member disposed with the shell component. The shell has a generally convex bone engaging outer surface and a generally concave inner surface. A groove is formed in the inner surface of the shell and extends about at least a portion of the inner circumference of the shell. The liner has an inner concave surface and an outer, convex surface with a shape complementary to and matable within the inner surface of the shell. One or more deformable tabs are formed on the locking member, adapted for securing the liner within the shell. The liner may be joined to the shell by press fitting the two components together such that the locking members engages one or more positive surface ridges on the liner.

24 Claims, 4 Drawing Sheets

ACETABULAR PROSTHESIS WITH RING LOCK MECHANISM

CROSS-REFERENCE TO RELATED APPLICATIONS

Not applicable.

STATEMENT REGARDING FEDERALLY SPONSORED RESEARCH

Not applicable.

FIELD OF THE INVENTION

The invention relates to joint prostheses and more particularly to acetabular prostheses useful for partial or total replacement of the hip joint.

BACKGROUND OF THE INVENTION

Acetabular prostheses are known for use as a component for a total hip prosthesis. Acetabular prostheses typically include two separate components, one of which is a cup or shell that is affixed within a cavity reamed in healthy bone of the acetabulum. The acetabular cup may have an external (i.e., bone-contacting) geometry that is appropriate for a given patient. The inner geometry of the acetabular cup is usually characterized by a smooth, generally spherical cavity. The acetabular cup is typically made of a metal or metal alloy. In some cases, however, polymeric acetabular cups are utilized.

A liner component is often mated with the inner geometry of the acetabular cup to provide a low friction bearing surface that articulates with a femoral head. The liner may have an outer, spherical surface that is of a size and shape to enable it to mate with the inner surface of the acetabular cup. The inner surface of the liner likewise is hemispherically shaped, having a smooth, low friction surface. As noted above, the femoral head seats within and articulates with the internal surface of the liner.

Acetabular cups are often made from a metal or metal alloy. Some designs, however, utilize polymeric cups. One polymer commonly used to form the liner is ultrahigh molecular weight polyethylene. However, it is also possible to fabricate the liner from other materials, including metals, metal alloys and ceramics.

Regardless of the materials and geometries used for the acetabular prosthesis, the acetabular cup and liner must be joined together, usually during the course of a surgical procedure. That is, a surgeon first implants the acetabular cup within the patient's acetabulum. Thereafter, the liner is separately affixed within the acetabular cup. A variety of liner designs exist and many are not symmetrical. Thus, the surgeon must determine the appropriate orientation of the liner with respect to the cup. Once the liner is properly oriented, it must remain so after affixation within the cup.

Some acetabular prosthesis designs do not permit easy mating of the liner to the cup; the mating of some designs can, in fact, be quite challenging. Specialized tools or separate components may be necessary to join these components or to permanently affix them together. In some instances the locking mechanism must be assembled during the surgical procedure. Such additional steps may render the attachment process more time-consuming and may introduce the possibility that the liner and the shell will become misaligned due to surgical technique or for other reasons. Further, there is always a possibility that the joinder mechanism may fail to achieve its objective to secure the two components to one another.

A number of patents describe acetabular prostheses designs that utilize a separate component to lock the liner and the shell together. Examples of such patents include U.S. Pat. Nos. 4,619,658; 4,770,658; 4,784,663; 4,969,910; 5,049,158; 5,171,285; 5,263,988; 5,425,779; 5,507,826; and 5,658,348.

Other known designs do not require a separate locking mechanism to join the liner and the cup. Instead, an interference fit or another form of mechanical engagement of the two components is relied upon. Examples of patents disclosing such attachment mechanisms include U.S. Pat. Nos. 4,172,296; 4,650,491; 5,376,122; 5,443,519; and 5,549,698.

Despite the acetabular prostheses designs that are known to exist, there is still a need for an acetabular prosthesis design that provides excellent attachment strength between the liner and the cup while at the same time providing ease of assembly without the need for additional assembly tools or components.

BRIEF SUMMARY OF THE INVENTION

An acetabular prosthesis has a shell component that is implantable within bone and a liner component that is matable to the shell. A locking member, housed within the shell, effectively and securely joins the liner and the shell together. The shell has a generally convex bone-engaging outer surface and a generally concave inner surface. At least one groove is formed in the inner surface of the shell and extends about at least a portion of the inner circumference of the shell. The liner has an inner concave surface and a outer, convex surface with a shape that is complimentary to and matable within the inner surface of the shell. The liner also includes at least one ridge that is elevated from the outer surface of the liner and extends about at least a portion of the circumference of the shell.

The locking member has a substantially circular base with at least one inwardly projecting, deformable tab member. Preferably, the locking member is preassembled within the shell to facilitate easy assembly of the acetabular prothesis during a surgical procedure.

The acetabular prosthesis may also have a structure to prevent rotation of the liner with respect to the shell after joinder of the two components. Such an anti-rotation mechanism may be in the form of one or more protrusions formed on the outer surface of the liner component. At least one cut-out region is formed in the shell with a size and shape complimentary to the protrusions such that each protrusion is matable within one of the recesses.

One advantage of the prosthesis of the invention lies in its ease of assembly and its ability to provide good attachment strength between the liner and the shell. Although the locking member helps to facilitate joinder of the liner in the shell, the locking member is advantageously pre-mounted within the shell to promote ease of assembly during a surgical procedure.

DETAILED DESCRIPTION OF THE INVENTION

Figure 1:
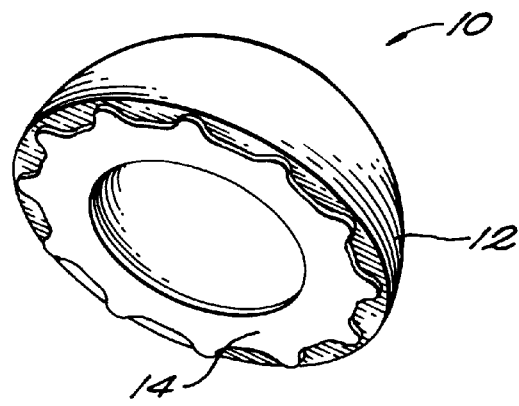
FIG. 1 is a perspective view of an acetabular prothesis according to the present invention in which an acetabular shell component is joined to a liner component.
Figure 2:
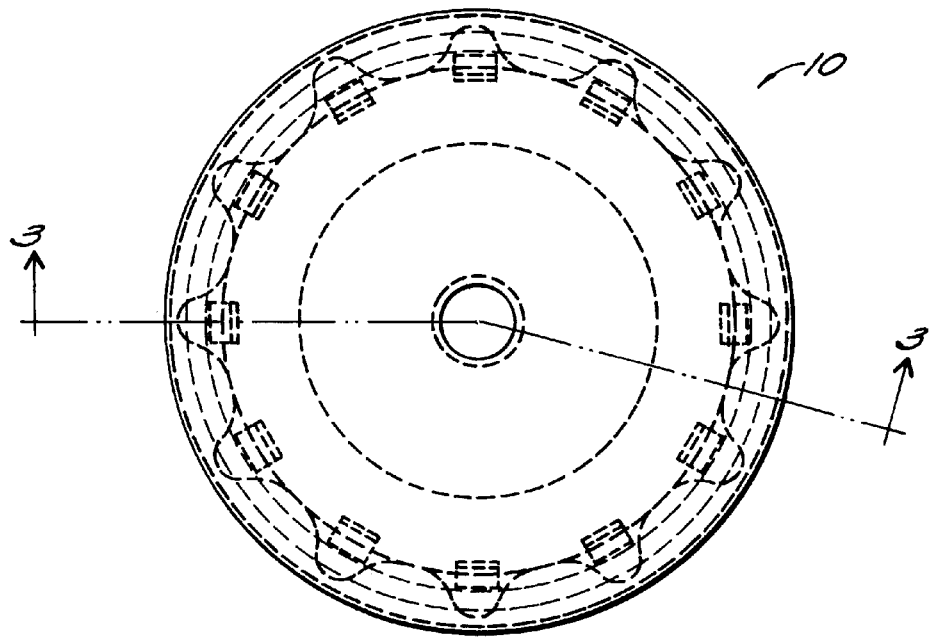
FIG. 2 is a top, plan view of the prothesis of FIG. 1.

The present invention provides an acetabular prosthesis with an effective and convenient locking mechanism for joining and securing the acetabular shell and liner components to each other. Referring to FIGS. 1–4, the acetabular prosthesis 10 includes an acetabular shell 12, a locking member 13 and a liner 14 which are attachable to one another through an interlocking engagement. Generally, the locking member 13 is mounted within the shell 12 and secures the liner 14 to the shell 12. Deformable tab members 100 disposed on the locking member 13 engage ridges 56 formed along the outer surface of the liner 14. A more detailed explanation of the interlocking engagement will follow after a discussion of the individual prosthesis components.

The acetabular shell 12, illustrated in FIGS. 5–8, is a substantially hemispherical member having a generally convex outer bone-engaging surface 16. Opposite the outer surface 16 is a generally hemispherical, substantially concave inner surface 18. The shell may be characterized as having an equator region 15 and a polar region 17. Further, the shell includes an equatorial axis 19 and a polar axis 21.

Figure 6:
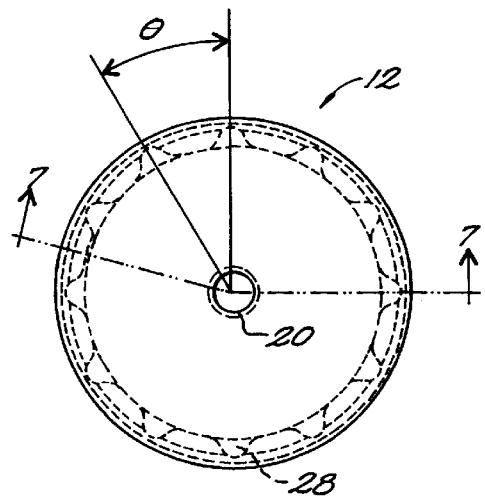
FIG. 6 is a top view of the shell component shown in FIG. 5.
Figure 7:
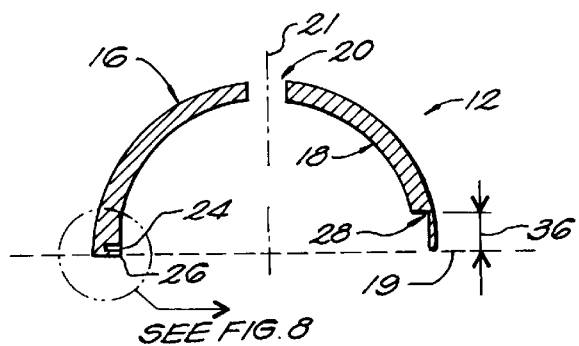
FIG. 7 is an elevated side view of the shell component shown in FIG. 6 at lines 7—7.

The outer surface 16, as shown in FIGS. 6 and 7, may include an apical hole 20 for seating an apical screw (not shown). One or more additional holes (not shown), effective to seat bone screws, may also extend through the outer surface 16. The outer surface 16 of the shell 12 may further include surface features (not shown), such as ridges, to optimize fixation to bone and/or to encourage bone ingrowth. One of ordinary skill in the art will readily appreciate that a variety of additional surface features, in addition to ridges, can be formed on the outer surface to optimize performance of the prosthesis.

Figure 8:
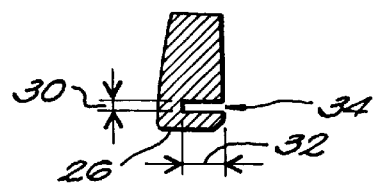
FIG. 8 is a detailed view of portion B shown in FIG. 7.
Figure 9:
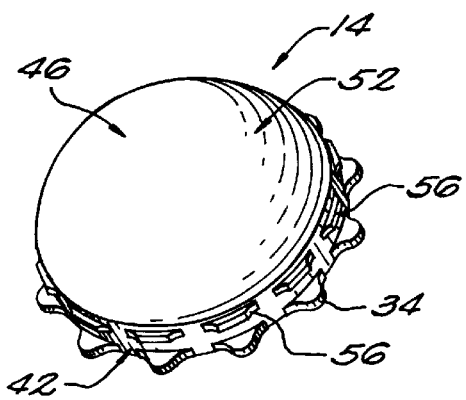
FIG. 9 is a perspective view of a liner component useful with the acetabular prosthesis of the invention.

The inner surface 18, as shown in FIGS. 7 and 8, includes a groove 24 that extends substantially parallel to the equatorial axis 19. The groove 24 may extend partially or entirely around the circumference of the shell 12, either continuously or in discrete sections. In the illustrated embodiment, the groove 24 is disposed in proximity to the equatorial region 15, and is spaced from the rim 26 of the shell 12. The groove 24 extends a distance from the inner surface 18 towards the outer surface 16 of the shell 12, in a plane parallel to the equatorial axis 19. The dimensions of the groove will vary depending upon variables such as the dimensions of the shell, the dimensions of the liner, the dimensions of certain surface features present on the liner, and the dimensions of the locking member.

In an exemplary embodiment, the groove 24 may have a height 30 in the range of about 0.6 to 1.7 mm and a depth 32 in the range of about 2 to 4 mm.

Further, the groove 24 is interrupted by cut-out regions 28, which extend perpendicular to the equatorial axis 19. The cut-out regions 28 are intended to seat both the deformable tab members 100 of the locking member 13, shown in FIGS. 13–15, and to mate with protrusions 34 present on the liner 14, as discussed below, to prevent rotation and movement of the liner 14 relative to the acetabular shell 12. The cut-out regions 28 extend from the rim 26 towards the polar region 17. The depth 36 of the cut-out regions 28 may be about 1.5 to 4 mm. The height 40 of the cut-out regions 28 may be in the range of about 2 to 8 mm and a width in the range of about 2 to 8 mm. The cut-out regions 28 may be separated from each other by an angle θ in the range of approximately 30° to 180°.

The shell 12 can be made from a variety of suitable materials. Generally, however, it is made from biocompatible metals or metal alloys known to those having ordinary skill in the art.

The liner 14, as shown in FIGS. 9 through 12, has an equatorial region 42 and a polar region 46. An equatorial axis 48 of the liner extends parallel to the equatorial region 42 while a polar axis 50 extends perpendicular to the equatorial axis 48. The liner 14 also has a convex outer surface 52, which is substantially hemispherically shaped and complementary to inner surface 18 of shell 12. Further, the liner 14 has a concave inner surface 54 which is intended to seat a femoral head of a hip prosthesis (not shown). One of ordinary skill in the art will appreciate that the inner surface 54 should be a smooth, low friction surface.

The liner 14 further includes one or more anti-rotation protrusions 34 which protrude from the outer surface 52 adjacent to the rim region 44. The protrusions 34 can be of virtually any shape that is complementary to and matable within the cut-out regions 28 of the shell 12. Protrusions 34 may be positioned at virtually any location on the outer surface 52 of the liner 14.

As noted above, the protrusions 34 on the liner 14 cooperate with the cut-out regions 28 in the shell 12 to prevent rotation of the liner 14 relative to the shell 12. No specific number of protrusions 34 and cut-out regions 28 is necessary to prevent rotation of the liner 14 relative to the shell 12 since any number will accomplish this objective. Generally, however, more than one protrusion is present and from four to twelve protrusions can be used, depending upon the size of the liner and the shell.

The outer surface 52 of the liner 14 also includes at least one raised ridge 56. In one embodiment, the ridge 56 protrudes from the outer surface 52 of the liner by a distance of about 0.5 to 1.5 mm. The ridge 56 may be a continuous structure, or it may be present on the outer surface of the liner in discrete sections. Further, the ridge 56 may extend partially or completely about the circumference of the liner, either continuously or in discrete sections.

Figure 12:
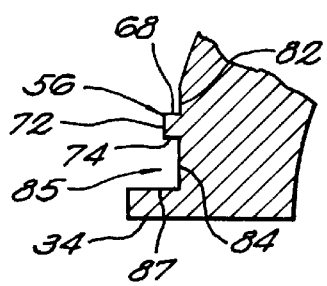
FIG. 12 is a detailed view of portion C shown in FIG. 11.

As shown in FIG. 12, the ridge 56 has a superior wall 68 which may be oriented substantially parallel with equatorial axis 48. Adjacent and inferior to superior wall 68 is an end wall 72. The end wall 72 may be substantially parallel to the polar axis 50. The ridge 56 terminates in an inferior wall 74 which, like the superior wall 68, may be substantially parallel to equatorial axis 48. In other embodiments, the superior wall 68 and/or inferior wall 74 may be disposed at an acute angle with respect to the end wall.

Figure 10:
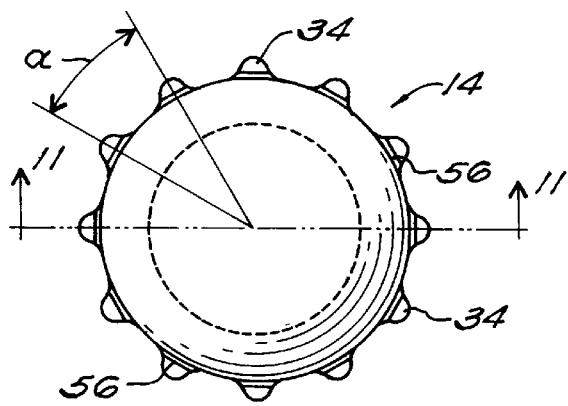
FIG. 10 is a top view of the liner component as shown in FIG. 9.
Figure 11:
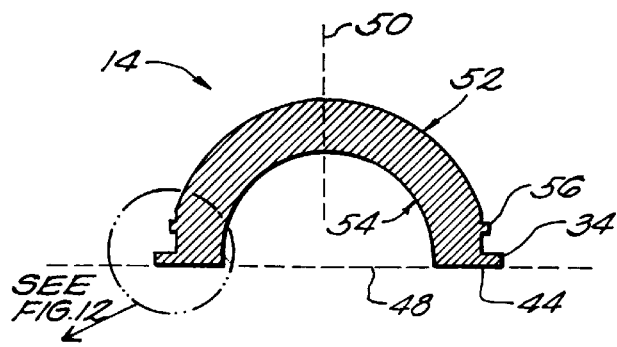
FIG. 11 is an elevated sectional view of the liner component shown in FIG. 10, at lines 11—11.

The dimensions of the ridge 56 and its various elements may vary depending upon the relative sizes of the shell 12, the locking member 13 and the liner 14 as well as the desired attachment strength. As noted above, a number of discrete ridges 56 may extend about the circumference of the outer surface 52 of the liner 12. FIG. 10 illustrates an embodiment where each ridge 56 is aligned with and superiorly disposed from protrusions 56 and extends about the circumference of the outer surface 52 at an angle α of approximately 30 degrees. One of ordinary skill in the art will appreciate that ridges 56 may be spaced apart from each other at a variety of alternative angles.

The ridge 56 may be integrally formed with the outer surface 52 of liner 14. In one embodiment, the ridge 56 is integral with a portion 82 of outer surface 52 that is superior to the rim region 44. The ridge 56 and the protrusion 34 cooperatively form a recess 85, at an inferior portion 84 of the liner 14, that is bound at an upper position by inferior wall 74 of the ridge 56 and at a lower position by a superior wall portion 87 of protrusion 34.

Figure 13:
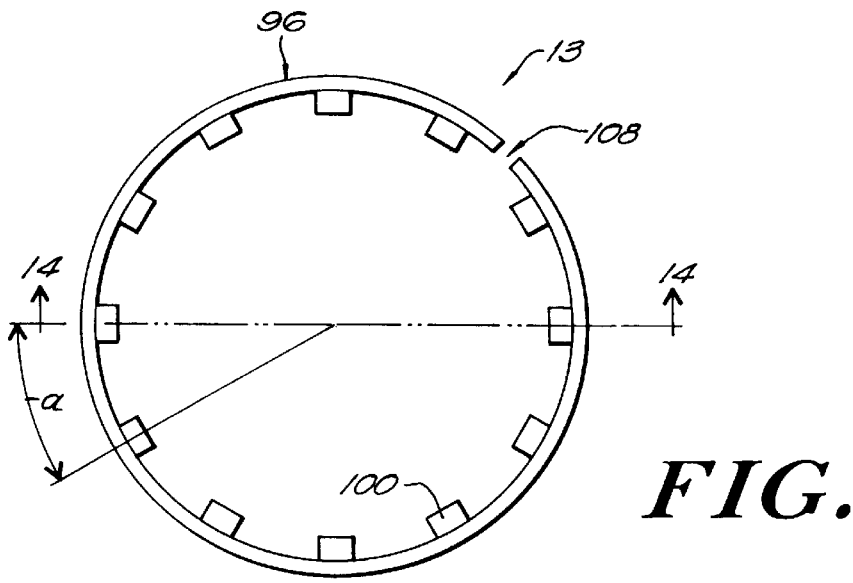
FIG. 13 is a plan view of a locking member useful with the prosthesis of the present invention.
Figure 14:
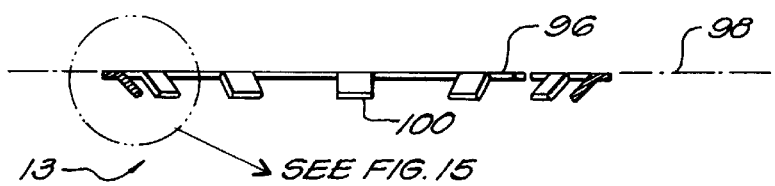
FIG. 14 is an elevated sectional view of the locking member of FIG. 13 at lines 14—14.
Figure 15:
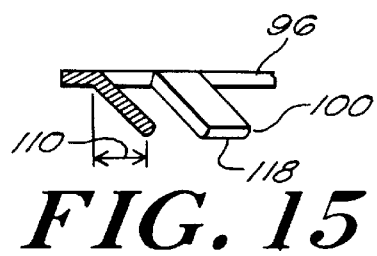
FIG. 15 is a detailed view of portion D of the locking member shown in FIG. 14.

Referring now to FIGS. 13, 14 and 15, the locking member 13 is shown having a substantially circular base 96 with at least one inwardly projecting, deformable tab member 100. The base 96 may be constructed of a flat wire or, in other embodiments, a round wire. The locking member 13 has an equatorial axis 98 which extends parallel to the equatorial axis 19 of the shell 12 when the locking member 13 is mounted within the shell 12. Preferably, the locking member 13 is preassembled within groove 24 of the shell to facilitate easy assembly of the acetabular prothesis during a surgical procedure. The base 96 further has an installation notch 108 to facilitate insertion of the locking member 13 within an acetabular shell. The notch 108 allows the base 96 to be partially deformed (i.e., radially compressed) to facilitate insertion of the locking member 13 within a shell component. The dimensions of the base will vary depending upon variables such as the dimensions of the shell and the dimensions of certain surface features present on the liner, such as the groove 24.

As further illustrated in FIG. 15, the deformable tab member 100 may be integrally formed with the circular base 96 of the locking member 13. The tab member 100 may be canted with respect to the equatorial axis 98 such that it extends superiorly (i.e., towards the polar region 17 of the shell 12). The tab members 100 may be oriented about the base 96 at an angle α in the range of approximately 20° to 90° with respect to one another. The length 110 of the tab member 100, which extends from the base 96 to the distal tip 118, is generally about 1.5 to 3.5 mm. One of ordinary skill in the art will appreciate that the deformable tab member 100 need not be overly pliable to effect insertion of the liner within the shell. It is also understood that the geometry of the tab members 100 may be modified to accommodate ease of insertion of a liner component.

Figure 16:
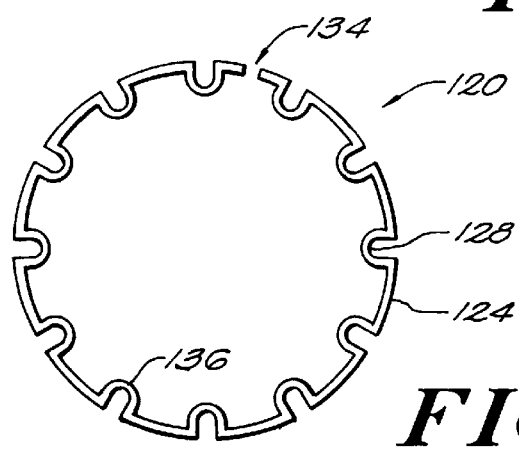
FIG. 16 is a plan view of an alternative locking member useful with the present invention.

The locking member 13 may assume additional configurations as well. For example, FIG. 16 illustrates a locking member 13 having a substantially circular base 124 that may be formed of a wire structure having a substantially circular cross section. The base 124 has at least one inwardly projecting deformable tab member 128. Each tab member 128 is integral with the base 124 and is of a substantially hemispherical shape. The base also has an installation notch 134 to facilitate insertion of the locking member 120 into an acetabular shell.

Figure 3:
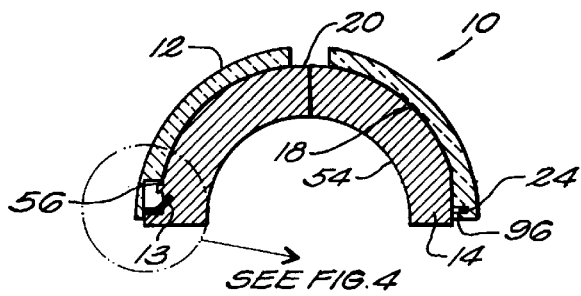
FIG. 3 is an elevated sectional view of the prothesis shown in FIG. 2, at lines 3—3.
Figure 4:
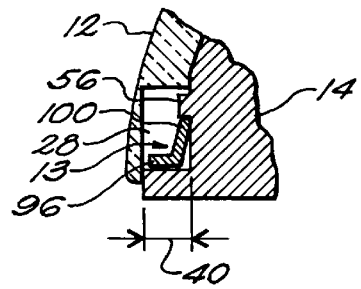
FIG. 4 is a detailed view of portion A of the prosthesis shown in FIG. 3.
Figure 5:
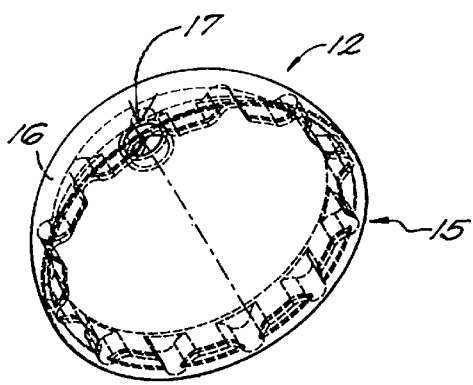
FIG. 5 is a perspective view of a shell component useful with the acetabular prosthesis of the invention.

A more detailed explanation of the interlocking engagement of the prosthesis components now follows. As shown in FIGS. 3 and 4, the invention provides a reliable and convenient attachment mechanism for selectively joining an acetabular shell to a liner component using an engaging locking member. To attach these two components together, the locking member 13 preferably is pre-mounted within the shell 12 as the locking member base 96 is disposed within groove 24 in the shell 12. As so assembled, the deformable tab members 100 are aligned with the cut-out regions 28 of the shell 12. In this configuration, the tab members 100 are angled towards the polar region 17 of the shell 12. The liner 14 is readied for placement into the shell 12 by aligning the protrusions 34 of the liner 14 with the cut-out regions 28 of the shell 12. This also operates to align the adjacent raised ridges 56 with the cut-out regions 28 of the shell 12 and with the tab members 100 of the locking member 13.

As the liner is pressed into the shell, the raised ridges encounter the deformable tabs causing some resistance. By applying additional force, the deformable tab members 100 pass over the end wall 72 of raised ridge 56 and reside as shown in FIG. 4 in inferior portion 84 of the liner 14. Such deformation allows the liner 14 and the ridges 56 to fit within the shell 12. Upon proper seating of the liner 14 within the shell 12, the deformable tab member 100 remains partially deformed, and engages the inferior wall 74 of the ridge 56, thereby securing the liner 14 to the shell 12. The amount of deformation of the tab member 100 during insertion and installation of a liner component will vary depending upon a variety of factors such as, for example, the dimensions of the liner and any surface features on the liner, the dimensions of the tab member, or material of the locking member.

One advantage of the prosthesis of the invention lies in its ease of assembly and its ability to provide good attachment strength between the liner and the shell. Although the locking ring helps to facilitate joinder of the liner in the shell, the locking member is advantageously pre-mounted within the shell to promote ease of assembly during a surgical procedure. The locking member also leads the liner toward the apex which may reduce micromotion and the generation of potential wear debris.

Having described the preferred embodiments of the invention, it will now become apparent to one of ordinary skill in the art that other embodiments incorporating their concepts may be used. It is felt therefore that these embodiments should not be limited to disclosed embodiments but rather should be limited only by the spirit and scope of the appended claims. All publications and references cited herein are expressly incorporated herein by reference in their entirety.

What is claimed is:

1. An acetabular shell assembly, comprising:
   a shell component having a generally convex bone-engaging outer surface extending between a rim region and a pole region and a generally concave inner surface having a circumferential groove extending about at least a portion of the circumference of the inner surface of the shell component, and at least one cut-out region;
   a liner component having a generally concave inner surface and a generally convex outer surface, wherein a rim region and a pole region of the outer surface of the liner have a shape complementary to and are matable within the inner surface of the shell component;

at least one raised ridge formed on the outer surface of the liner component;

at least one protrusion formed on the outer surface of the liner component, each of the at least one protrusions being matable within one of the at least one cut-out regions of the shell component; and a locking member having a substantially circular base with at least one inwardly projecting, deformable tab member, the locking member being mountable within the circumferential groove of the shell component.

2. The assembly of claim 1, wherein the groove extends about the entire circumference of the inner surface of the shell component.

3. The assembly of claim 2, wherein each of the at least one tab members is oriented to project towards the pole region of the shell component when the locking member is mounted in the circumferential groove.

4. The assembly of claim 3, wherein each of the at least one tab members protrude from the base by a distance in the range of about 1.5 to 3.5 mm.

5. The assembly of claim 4, wherein the distance by which the at least one tab member protrudes from the base is less than the height of the at least one cut-out region.

6. The assembly of claim 1, wherein each of the at least one cut-out regions intersects the circumferential groove.

7. The assembly of claim 1, wherein the at least one cut-out region has a height in the range of about 1.5 to 4 mm.

8. The assembly of claim 7, wherein the at least one cut-out region has a depth in the range of about 2 to 8 mm.

9. The assembly of claim 8, wherein the at least one cut-out region has a width in the range of about 2 to 8 mm.

10. The assembly of claim 1, wherein the locking member base is selected from the group consisting of a flat wire and a round wire.

11. The assembly of claim 10, wherein the base is a flat wire that is oriented in a plane extending parallel to a plane of the rim region of the shell component when the base is mounted within the circumferential groove.

12. The assembly of claim 1, wherein the liner component has a plurality of raised ridges, each raised ridge being adjacent to one of the at least one protrusions.

13. The assembly of claim 1, wherein each of the at least one protrusions is formed adjacent to the rim region of the shell.

14. The assembly of claim 1 wherein each of the at least one raised ridge protrudes from the outer surface of the liner by a distance of about 0.5 to 1.5 mm.

15. The assembly of claim 14 wherein each of the at least one raised ridges has an end wall, a superior wall substantially perpendicular to the end wall, and an inferior wall that is disposed at an acute angle with respect to end wall.

16. The assembly of claim 15 wherein the inferior wall is disposed at an angle in the range of about 0° to 45° with respect to the end wall.

17. The assembly of claim 15 wherein the liner component and the shell component are matable to one another by aligning the at least one protrusion with the at least one cut-out region and forcing the liner component within the shell component such that the at least one ridge deforms the at least one tab members until the tab member positively engages the inferior wall.

18. The assembly of claim 1 wherein the at least one raised ridge extends continuously about the entire circumference of the outer surface of the liner component.

19. The assembly of claim 1, wherein the locking member has an installation notch formed along the circular base.

20. The assembly of claim 1, wherein the groove has a height in the range of about 0.6 to 1.7 mm.

21. The assembly of claim 20, wherein the groove has a depth in the range of about 2 to 4 mm.

22. An acetabular shell assembly, comprising:

a shell component having a generally convex bone-engaging outer surface extending between a rim region and a pole region and a generally concave inner surface having a circumferential groove extending about at least a portion of the circumference of the inner surface of the shell component, and at least one cut-out region;

a liner component having a generally concave inner surface and a generally convex outer surface, wherein a rim region and a pole region of the outer surface of the liner have a shape complementary to and are matable within the inner surface of the shell component;

at least one raised ridge formed on the outer surface of the liner component;

a locking member having a substantially circular base with at least one inwardly projecting, deformable tab member, the locking member being mountable within the circumferential groove of the shell component.

23. The assembly of claim 22 further comprising at least one protrusion formed on the outer surface of the liner component, each of the at least one protrusions being matable within one of the at least one cut-out regions of the shell component.

24. The assembly of claim 22, wherein the locking member has an installation notch formed along the circular base.

* * * * *